United States Patent
Forssmann et al.

(10) Patent No.: US 6,939,851 B1
(45) Date of Patent: Sep. 6, 2005

(54) SERINE PROTEINASE INHIBITORS

(75) Inventors: Wolf-Georg Forssmann, Hannover (DE); Hans-Jürgen Mägert, Hannover (DE); Ludger Ständker, Hannover (DE); Peter Kreutzmann, Magdeburg (DE)

(73) Assignee: Pharis Biotec GmbH, Hanover (GB)

(*) Notice: Subject to any disclaimer, the term of this patent is extended or adjusted under 35 U.S.C. 154(b) by 0 days.

(21) Appl. No.: 09/926,820

(22) PCT Filed: Jun. 22, 1999

(86) PCT No.: PCT/EP99/04331
§ 371 (c)(1),
(2), (4) Date: May 6, 2002

(87) PCT Pub. No.: WO00/78963
PCT Pub. Date: Dec. 28, 2000

(51) Int. Cl.[7] .......................... A61K 38/00; C07K 14/00

(52) U.S. Cl. .......................................... 514/12; 530/350
(58) Field of Search ............................ 514/44; 530/350; 424/94.64

(56) References Cited

FOREIGN PATENT DOCUMENTS

| WO | WO 98/46758 | 10/1998 |
|---|---|---|
| WO | WO 99/31117 | 6/1999 |
| WO | WO 99/33974 | 7/1999 |
| WO | WO 00/78963 A1 | 12/2000 |

OTHER PUBLICATIONS

International Search Report—PCT/US98/27059.

*Primary Examiner*—Robert A. Wax
*Assistant Examiner*—Suzanne M. Mayer
(74) *Attorney, Agent, or Firm*—Jacobson Holman PLLC

(57) ABSTRACT

The invention relates to serine protease inhibitors having the amino acid sequence in accordance with Seq. ID No. 1.

4 Claims, 4 Drawing Sheets

FIG. 1A

```
Frame 2                                                       M   K   I   A
         ATG CAT GGA GTG GAC CTG TAG GCG ACT TGC ATC GTC TTC AAC ATG AAG ATA GCC
                  10          19          28          37          46          55

|--> HF 6479
 T   V   S   V   L   L   P   L   A   L   C   L   I   Q   D   A   A   S | K   N
ACA GTG TCA GTG CTT CTG CCC TTG GCT CTT TGC CTC ATA CAA GAT GCT GCC AGT AAG AAT
         64          73          82          91         100         109

Repeat 1
             *                                                           #
 E   D   Q   E   M   C   H   E   F   Q   A   F   M   K   N   G   K   L   F   C
GAA GAT CAG GAA ATG TGC CAT GAA TTT CAG GCA TTT ATG AAA AAT GGA AAA CTG TTC TGT
             124         133         142         151         160         169
                                                                     #
 P   Q   D   K   K   F   F   Q   S   L   D   G   I   M   F   I   N   K   C   A
CCC CAG GAT AAG AAA TTT TTT CAA AGT CTT GAT GGA ATA ATG TTC ATC AAT AAA TGT GCC
             184         193         202         211         220         229

*                                   HF 6479 <--|
 T   C   K   M   I   L   E   K   E   A   K   S   Q | K   R   A   R   H   L   A
ACG TGC AAA ATG ATA CTG GAA AAA GAA GCA AAA TCA CAG AAG AGG GCC AGG CAT TTA GCA
             244         253         262         271         280         289 typical Kazal domain 1
                                                 *
 R   A   P   K   A   T   A   P   T   E   L   N   C   D   D   F   K   K   G   E
AGA GCT CCC AAG GCT ACT GCC CCA ACA GAG CTG AAT TGT GAT GAT TTT AAA AAA GGA GAA
             304         313         322         331         340         349
                         #                                +
 R   D   G   D   F   I   C   P   D   Y   Y   E   A   V   C   G   T   D   G   K
AGA GAT GGG GAT TTT ATC TGT CCT GAT TAT TAT GAA GCT GTT TGT GGC ACA GAT GGG AAA
             364         373         382         391         400         409
     !                   #               *
 T   Y   D   N   R   C   A   L   C   A   E   N   A   K   T   G   S   Q   I   G
ACA TAT GAC AAC AGA TGT GCA CTG TGT GCT GAG AAT GCG AAA ACC GGG TCC CAA ATT GGT
             424         433         442         451         460         469

+                                Repeat 2
                                                              *
 V   K   S   E   G   E   C   K   S   S   N   P   E   Q   D   V   C   S   A   F
GTA AAA AGT GAA GGG GAA TGT AAG AGC AGT AAT CCA GAG CAG GAT GTA TGC AGT GCT TTT
             484         493         502         511         520         529

R   P   F   V   R   D   G   R   L   G   C   T   R   E   N   D   P   V   L   G
CGG CCC TTT GTT AGA GAT GGA AGA CTT GGA TGC ACA AGG GAA AAT GAT CCT GTT CTT GGT
             544         553         562         571         580         589
                                         #               *
 P   D   G   K   T   H   G   N   K   C   A   M   C   A   E   L   F   L   K   E
CCT GAT GGG AAG ACG CAT GGC AAT AAG TGT GCA ATG TGT GCT GAG CTG TTT TTA AAA GAA
             604         613         622         631         640         649

A   E   N   A   K   R   E   G   E   T   R   I   R   R   N   A   E   K   D   F
GCT GAA AAT GCC AAG CGA GAG GGT GAA ACT AGA ATT CGA CGA AAT GCT GAA AAG GAT TTT
             664         673         682         691         700         709

Repeat 3
*                                                        #
 C   K   E   Y   E   K   Q   V   R   N   G   R   L   F   C   T   R   E   S   D
TGC AAG GAA TAT GAA AAA CAA GTG AGA AAT GGA AGG CTT TTT TGT ACA CGG GAG AGT GAT
             724         733         742         751         760         769
                                                         #           *
 P   V   R   G   P   D   G   R   M   H   G   N   K   C   A   L   C   A   E   I
CCA GTC CGT GGC CCT GAC GGC AGG ATG CAT GGC AAC AAA TGT GCC CTG TGT GCT GAA ATT
             784         793         802         811         820         829

F   K   R   R   F   S   E   E   N   S   K   T   D   Q   N   L   G   K   A   E
TTC AAG CGG CGT TTT TCA GAG GAA AAC AGT AAA ACA GAT CAA AAT TTG GGA AAA GCT GAA
             844         853         862         871         880         889

Repeat 4
                                                 *
 E   K   T   K   V   K   R   E   I   V   K   L   C   S   Q   Y   Q   N   Q   A
GAA AAA ACT AAA GTT AAA AGA GAA ATT GTG AAA CTC TGC AGT CAA TAT CAA AAT CAG GCA
             904         913         922         931         940         949
```

FIG. 1B

```
     K   N   G   I   L   F   C   T   R   E   N   D   P   I   R   G   P   D   G   K
    AAG AAT GGA ATA CTT TTC TGT ACC AGA GAA AAT GAC CCT ATT CGT GGT CCA GAT GGG AAA
             964         973         982         991        1000        1009

M   H   G   N   L   C   S   M   C   Q   V   Y   F   Q   A   E   N   E   E   K
    ATG CAT GGC AAC TTG TGT TCC ATG TGT CAA GTC TAC TTC CAA GCA GAA AAT GAA GAA AAG
            1024        1033        1042        1051        1060        1069

|---> HF 7665
     K   K   A   E   A   R   A   R   N   K   R   E   S   G   K   A   T   S   Y   A
    AAA AAG GCT GAA GCA CGA GCT AGA AAC AAA AGA GAA TCT GGA AAA GCA ACC TCA TAT GCA
            1084        1093        1102        1111        1120        1129

Repeat 5
     E   L   C   N   E   Y   R   K   L   V   R   N   G   K   L   A   C   T   R   E
    GAG CTT TGC AAT GAA TAT CGA AAG CTT GTG AGG AAC GGA AAA CTT GCT TGC ACC AGA GAG
            1144        1153        1162        1171        1180        1189

N   D   P   I   Q   G   P   D   G   K   V   H   G   N   T   C   S   M   C   E
    AAC GAT CCT ATC CAG GGC CCA GAT GGG AAA GTG CAC GGC AAC ACC TGC TCC ATG TGT GAG
            1204        1213        1222        1231        1240        1249

HF 7665 <---|
     V   F   F   Q   A   E   E   E   E   K   K   K   K   E   G   E   S   R   N   K
    GTC TTC TTC CAA GCA GAA GAA GAA GAA AAG AAA AAG AAG GAA GGC GAA TCA AGA AAC AAA
            1264        1273        1282        1291        1300        1309

Repeat 6
     R   Q   S   K   S   T   A   S   F   E   E   L   C   S   E   Y   R   K   S   R
    AGA CAA TCT AAG AGT ACA GCT TCC TTT GAG GAG TTG TGT AGT GAA TAC CGC AAA TCC AGG
            1324        1333        1342        1351        1360        1369

K   N   G   R   L   F   C   T   R   E   N   D   P   I   Q   G   P   D   G   K
    AAA AAC GGA CGG CTT TTT TGC ACC AGA GAG AAT GAC CCC ATC CAG GGC CCA GAT GGG AAA
            1384        1393        1402        1411        1420        1429

M   H   G   N   T   C   S   M   C   E   A   F   F   Q   Q   E   E   R   A   R
    ATG CAT GGC AAC ACC TGC TCC ATG TGT GAG GCC TTC TTT CAA CAA GAA GAA AGA GCA AGA
            1444        1453        1462        1471        1480        1489

Repeat 7
     A   K   A   K   R   E   A   A   K   E   I   C   S   E   F   R   D   Q   V   R
    GCA AAG GCT AAA AGA GAA GCT GCA AAG GAA ATC TGC AGT GAA TTT CGG GAC CAA GTG AGG
            1504        1513        1522        1531        1540        1549

N   G   T   L   I   C   T   R   E   H   N   P   V   R   G   P   D   G   K   M
    AAT GGA ACA CTT ATA TGC ACC AGG GAG CAT AAT CCT GTC CGT GGA CCA GAT GGC AAA ATG
            1564        1573        1582        1591        1600        1609

H   G   N   K   C   A   M   C   A   S   V   F   K   L   E   E   E   E   K   K
    CAT GGA AAC AAG TGT GCC ATG TGT GCC AGT GTG TTC AAA CTT GAA GAA GAA GAG AAG AAA
            1624        1633        1642        1651        1660        1669

N   D   K   E   E   K   G   K   V   E   A   E   K   V   K   R   E   A   V   Q
    AAT GAT AAA GAA GAA AAA GGG AAA GTT GAG GCT GAA AAA GTT AAG AGA GAA GCA GTT CAG
            1684        1693        1702        1711        1720        1729

Repeat 8
     E   L   C   S   E   Y   R   H   Y   V   R   N   G   R   L   P   C   T   R   E
    GAG CTG TGC AGT GAA TAT CGT CAT TAT GTG AGG AAT GGA CGA CTC CCC TGT ACC AGA GAG
            1744        1753        1762        1771        1780        1789

N   D   P   I   E   G   L   D   G   K   I   H   G   N   T   C   S   M   C   E
    AAT GAT CCT ATT GAG GGT CTA GAT GGG AAA ATC CAC GGC AAC ACC TGC TCC ATG TGT GAA
            1804        1813        1822        1831        1840        1849

A   F   F   Q   Q   E   A   K   E   K   E   R   A   E   P   R   A   K   V   K
    GCC TTC TTC CAG CAA GAA GCA AAA GAA AAA GAA AGA GCT GAA CCC AGA GCA AAA GTC AAA
            1864        1873        1882        1891        1900        1909

Repeat 9
     R   E   A   E   K   E   T   C   D   E   F   R   R   L   L   Q   N   G   K   L
```

FIG. 1C

```
    AGA GAA GCT GAA AAG GAG ACA TGC GAT GAA TTT CGG AGA CTT TTG CAA AAT GGA AAA CTT
        1924        1933        1942        1951        1960        1969
     #
     F   C   T   R   E   N   D   P   V   R   G   P   D   G   K   T   H   G   N   K
    TTC TGC ACA AGA GAA AAT GAT CCT GTG CGT GGC CCA GAT GGC AAG ACC CAT GGC AAC AAG
        1984        1993        2002        2011        2020        2029
    #            *
     C   A   M   C   K   A   V   F   Q   K   E   N   E   E   R   K   R   K   E   E
    TGT GCC ATG TGT AAG GCA GTC TTC CAG AAA GAA AAT GAG GAA AGA AAG AGG AAA GAA GAG
        2044        2053        2062        2071        2080        2089

E   D   Q   R   N   A   G   H   G   S   S   G   G   G   G   N   T   Q
    GAA GAT CAG AGA AAT GCT GCA GGA CAT GGT TCC AGT GGT GGT GGA GGA GGA AAC ACT CAG
        2104        2113        2122        2131        2140    |   2149

Repeat 10
         *                                                                 #
     D   E   C   A   E   Y   Q   E   Q   M   K   N   G   R   L   S   C   T   R   E
    GAC GAA TGT GCT GAG TAT CAG GAA CAA ATG AAA AAT GGA AGA CTC AGC TGT ACT CGG GAG
        2164        2173        2182        2191        2200        2209
                                                                #              *
     S   D   P   V   R   D   A   D   G   K   S   Y   N   N   Q   C   T   M   C   K
    AGT GAT CCT GTA CGT GAT GCT GAT GGC AAA TCG TAC AAC AAT CAG TGT ACC ATG TGT AAA
        2224        2233        2242        2251        2260        2269

A   K   L   E   R   E   A   E   R   K   N   E   Y   S   R   S   R   S   N   G
    GCA AAA TTG GAA AGA GAA GCA GAG AGA AAA AAT GAG TAT TCT CGC TCC AGA TCA AAT GGG
        2284        2293        2302        2311        2320        2329

Repeat 11
                                                 *
     T   G   S   E   S   G   K   D   T   C   D   E   F   R   S   Q   M   K   N   G
    ACT GGA TCA GAA TCA GGG AAG GAT ACA TGT GAT GAG TTT AGA AGC CAA ATG AAA AAT GGA
        2344        2353        2362        2371        2380        2389
             #
     K   L   I   C   T   R   E   S   D   P   V   R   G   P   D   G   K   T   H   G
    AAA CTT ATC TGC ACT CGA GAA AGT GAC CCT GTC CGG GGT CCA GAT GGC AAG ACA CAT GGT
        2404        2413        2422        2431        2440        2449
                 #       *
     N   K   C   T   M   C   K   E   K   L   E   R   E   A   A   E   K   K   K   K
    AAT AAG TGT ACT ATG TGT AAG GAA AAA CTG GAA AGG GAA GCA GCT GAA AAA AAA AAG AAA
        2464        2473        2482        2491        2500        2509

E   D   E   D   R   S   N   T   G   E   R   S   N   T   G   E   R   S   N   D
    GAG GAT GAA GAC AGG AGC AAT ACA GGA GAA AGG AGC AAT ACA GGA GAA AGG AGC AAT GAC
        2524        2533        2542        2551        2560        2569

Repeat 12
         *                                                                 #
     K   E   D   L   C   R   E   F   R   S   M   Q   R   N   G   K   L   I   C   T
    AAA GAG GAT CTG TGT CGT GAA TTT CGA AGC ATG CAG AGA AAT GGA AAG CTT ATC TGC ACC
        2584        2593        2602        2611        2620        2629
                                                                             #
     R   E   N   N   P   V   R   G   P   Y   G   K   M   H   I   N   K   C   A   M
    AGA GAA AAT AAC CCT GTT CGA GGC CCA TAT GGC AAG ATG CAC ATC AAT AAA TGT GCT ATG
        2644        2653        2662        2671        2680        2689
    *
     C   Q   S   I   F   D   R   E   A   N   E   R   K   K   K   D   E   E   K   S
    TGT CAG AGC ATC TTT GAT CGA GAA GCT AAT GAA AGA AAA AAG AAA GAT GAA GAG AAA TCA
        2704        2713        2722        2731        2740        2749

Repeat 13
                                                         *
     S   S   K   P   S   N   N   A   K   D   E   C   S   E   F   R   N   Y   I   R
    AGT AGC AAG CCC TCA AAT AAT GCA AAG GAT GAG TGC AGT GAA TTT CGA AAC TAT ATA AGG
        2764        2773        2782        2791        2800        2809
                         #
     N   N   E   L   I   C   P   R   E   N   D   P   V   H   G   A   D   G   K   F
    AAC AAT GAA CTC ATC TGC CCT AGA GAG AAT GAC CCA GTG CAC GGT GCT GAT GGA AAG TTC
        2824        2833        2842        2851        2860        2869
                 #       *
     Y   T   N   K   C   Y   M   C   R   A   V   F   L   T   E   A   L   E   R   A
    TAT ACA AAC AAG TGC TAC ATG TGC AGA GCT GTC TTT CTA ACA GAA GCT TTG GAA AGG GCA
        2884        2893        2902        2911        2920        2929

K   L   Q   E   K   P   S   H   V   R   A   S   Q   E   E   D   S   P   D   S
    AAG CTT CAA GAA AAG CCA TCC CAT GTT AGA GCT TCT CAA GAG GAA GAC AGC CCA GAC TCT
        2944        2953        2962        2971        2980        2989
                                typical Kazal domain 2
```

FIG. 1D

```
  F    S    S    L    D    S    E    M    C    K    D    Y    R    V    L    P    R    I    G    Y
 TTC  AGT  TCT  CTG  GAT  TCT  GAG  ATG  TGC  AAA  GAC  TAC  CGA  GTA  TTG  CCC  AGG  ATA  GGC  TAT
      3004           3013           3022           3031           3040           3049
  L    C    P    K    D    L    K    P    V    C    G    D    D    G    Q    T    Y    N    N    P
 CTT  TGT  CCA  AAG  GAT  TTA  AAG  CCT  GTC  TGT  GGT  GAC  GAT  GGC  CAA  ACC  TAC  AAC  AAT  CCT
      3064           3073           3082           3091           3100           3109
  C    M    L    C    H    E    N    L    I    R    Q    T    N    T    H    I    R    S    T    G
 TGC  ATG  CTC  TGT  CAT  GAA  AAC  CTG  ATA  CGC  CAA  ACA  AAT  ACA  CAC  ATC  CGC  AGT  ACA  GGG
      3124           3133           3142           3151           3160           3169
  K    C    E    E    S    S    T    P    G    T    T    A    A    S    M    P    P    S    D    E
 AAG  TGT  GAG  GAG  AGC  AGC  ACC  CCA  GGA  ACC  ACC  GCA  GCC  AGC  ATG  CCC  CCG  TCT  GAC  GAA
      3184           3193           3202           3211           3220           3229

TGA  CAG  GAA  GAT  TGT  TGA  AAG  CCA  TGA  GGG  AAA  AAA  TAA  ACC  CCA  GTT  CTG  AAT  CAC  CTA
      3244           3253           3262           3271           3280           3289

CCT  TCA  CCA  TCT  GTA  TAT  ACA  AAG  AAT  TCT  TCG  GAG  CTT  GTC  TTA  TTT  GCT  ATA  GAA  AAC
      3304           3313           3322           3331           3340           3349

AAT  ACA  GAG  CTT  TTG  GGA  ATG  GAA  TCA  CTG  ATT  TTC  AGT  CTT  TTC  CAT  TTC  TTT  CCT  CCT
      3364           3373           3382           3391           3400           3409

AGA  ATC  TGT  GAT  CTG  AGG  GTA  TAA  AGA  CAT  TTC  CAC  CAA  GTT  TGA  GCC  CTC  AAA  ATG  TCC
      3424           3433           3442           3451           3460           3469
                                                    polyadenylation signal
 TGA  TTA  CAA  TGC  TGT  CTG  TCC  AAC  TGC  CTG  TTC  AAT  AAA  AGT  AAA  CTC  AGC  AGA  AAA....
      3484           3493           3502           3511           3520           3529

......poly(A) tail
```

The following sequence corrections have been performed:

An additional A in position 2510 results in a frame shift which produces three additional inhibitor domains.

Base were exchanged in ten different positions:

Position  551:  G for A
Position 1207:  C for T
Position 1258:  C for T
Position 1261:  C for T
Position 2175:  A for G
Position 2950:  G for A
Position 3228:  C for T
Position 3284:  C for T
Position 3324:  C for T
Position 3337:  C for T

SEQUENZPROTOKOLL

<110> Forssmann Prof., Wolf-Georg

<120> Serin-Proteinase-Inhibitoren

<130> Forssmann

<140>
<141>

<160> 12

<170> PatentIn Ver. 2.1

<210> 1

SERINE PROTEINASE INHIBITORS

The present invention relates to serine protease inhibitors, cDNA coding for serine protease inhibitors, medicaments containing such inhibitors or their coding nucleic acid, use of the compounds according to the invention for the preparation of medicaments for the treatment of various indications, antibodies or antibody fragments against epitopes of the compounds according to the invention, poly- or oligonucleotides which will hybridize to genes of the compounds according to the invention, a diagnostic agent for detecting the compounds according to the invention, and medicaments containing antibodies or poly- or oligonucleotides according to the invention.

Proteolytic processes play an important physiological role in all organisms; a distinction has to be made between non-specific and specific proteolytic reactions. The former include, for example, the digestion of food in the digestive tract by endopeptidases, and the intracellular degradation of used endogenous substances and phagocytosed materials by lysosomal proteases. Specific proteolyses mostly serve for the conversion of a proenzyme to its active form, as in the conversion of trypsinogen to trypsin, and of chymotrypsinogen to chymotrypsin, and in the callicrein-kinin cascades and the blood clotting cascade. Depending on the structure of the reactive site of the proteinases involved, they are classified into the classes of serine proteases (e.g., chymotrypsin, trypsin, elastase and cathepsin G), aspartate proteases (e.g., cathepsin D, cathepsin E and pepsin), cysteine proteases (e.g., cathepsin B, cathepsin H and cathepsin L), and the metallo-proteases (e.g., collagenase and thermolysin).

In order to be able to correct the proteolytic processes which often proceed in a cascade, the organisms is provided with a number of other proteins, the protease inhibitors (for a survey, see Laskowski and Kato, 1980, and Bode and Huber, 1992). Thus, the liver-synthesized human plasma protease inhibitors $\alpha_1$-antichymotrypsin and $\alpha_1$-proteinase inhibitors protect the lung tissue from non-specific attack by the proteinases cathepsin G and elastase from polymorphonuclear lymphocytes. When the balance between proteases and their specific inhibitors is disturbed, pathological effects may arise. For example, an excess ratio of elastase to $\alpha_1$-proteinase inhibitor increases the risk of formation of a lung emphysema by a factor of about 20 to 30 in patients with a genetically caused deficiency in this factor as compared to the normal population (Carrel and Owen, 1980). With smokers, the formation of an emphysema is promoted by oxidation of the amino acid methionine which is present in the reactive site of the $\alpha_1$-proteinase inhibitor by oxidants contained in cigarette smoke (Miller and Kuschner, 1969; Ohlsson et al., 1980). Also in the case of infection with Gram-negative bacteria, their endotoxins can cause disintegration of phagocytes and thus the secretion of lysosomal proteases, which may cause an uncontrolled damage to tissues and inflammations due to the increased consumption of protease inhibitors. For this reason, certain protease inhibitors have a high therapeutic potential (see, e.g., Fritz, 1980).

International Application PCT/EP 98/08424 relates to serine protease inhibitors, wherein said serine protease inhibitors have a domain with four cysteines, and a sequence of from 0 to 20 amino acids is present between the first and second cysteines, or said serine protease inhibitors have a domain of six cysteines, and a sequence of from 7 to 20 amino acids is present between the first and second cysteines.

BRIEF SUMMARY OF THE INVENTION

It has been the object of the present invention to provide further serine protease inhibitors.

This object is achieved by a serine protease inhibitor having the amino acid sequence according to SEQ ID NO: 1.

The present invention also relates to fragments of the serine protease inhibitor according to the invention having the amino acid sequence $R_1$—X—$R_2$, wherein $R_1$ is $NH_2$, an amino acid or a peptide with up to 100 amino acids, and $R_2$ is COOH, $CONH_2$, an amino acid or a peptide with up to 100 amino acids, and X is selected from SEQ ID NOS: 2 to 6.

It is preferred that the serine protease inhibitor contains one or more disulfide bridges. It is particularly preferred for it to contain a disulfide bridge between the first and fourth cysteines and/or between the second and third cysteines, or to contain a disulfide bridge between the first and fifth cysteines and/or between the second and fourth cysteines and/or between the third and sixth cysteines.

In addition to the amino acid sequence of the preferred compounds according to the invention, further information about the cDNA coding for the compounds according to the invention can also be seen from FIG. 1. In particular, the corresponding motifs and primer-hybridizing sites are indicated.

BRIEF DESCRIPTION OF THE DRAWING

FIG. 1 illustrates, in addition to the amino acid sequence of the preferred compounds according to the invention, further information about the cDNA coding for the compounds according to the invention. In particular, the corresponding motifs and primer- hybridizing sites are indicated.

According to the invention, nucleic acids coding for the compounds according to the invention, especially a DNA having the nucleic acid sequence according to SEQ ID NOS: 7 to 12, are also claimed.

The compounds according to the invention are useful as medicaments. In this case, they are administered together with pharmaceutically acceptable vehicles.

The medicaments according to the invention containing the protease inhibitors according to the invention are preferably administered in amounts of from 1 to 100 mg/kg of the patient's body weight. As the dosage form, all galenic formulations for peptide active substances may be used. The medicaments containing nucleic acids according to the invention are preferably administered in amounts of from 0.1 to 100 mg/kg of body weight of a corresponding patient. In this case, the galenic dosage forms which may be used are those which are suitable for the administration of nucleic acids without rendering the nucleic acids ineffective by metabolic influences before they have reached their site of action. For example, liposomes in which the nucleic acids are contained can be employed as a galenic dosage form.

The compounds according to the invention can be used, in particular, for the treatment of acute or chronic cervix inflammations, inflammations of Bartholin's gland or other vaginal regions, tonsillitis, pharyngitis and laryngitis, acute or chronic inflammatory processes accompanied by excessive formation of mucus and the resulting acute emergency situations, postoperative bleedings due to hyperfibrinolysis, and for the prophylaxis of lung emphysema formation in deficiencies of $\alpha_1$-proteinase inhibitor.

Further, they may be employed for the therapy of asthma, AIDS, tumor diseases and leukemia.

The compounds according to the invention can be administered in deficiencies of serine protease inhibitors to correct endogenous defects. The nucleic acids may also be used in gene therapy, either directly or coupled to suitable vehicles. Suitable vectors include, in particular, attenuated adenoviruses into which the corresponding genes have been incorporated.

The polypeptides according to the invention can serve for the preparation of antibodies or antibody fragments. These are simply prepared by the immunization of appropriate mammals. By per se known operations, the antibodies may also be humanized so that such antibodies can also be employed for therapeutic use. Antibodies or antibody fragments can then by employed for the regulation of diseases in which the protease inhibitors are expressed in a pathological way. Also, antisense nucleic acids complementary to the nucleic acids according to the invention may be employed in therapeutical use in overexpressions of the protease inhibitor genes.

The compounds according to the invention can be easily prepared by per se known methods of peptide or nucleotide synthesis. Preparation of the compounds by genetic engineering is also possible.

Those skilled in the art will recognize that fragments of the polypeptides according to the invention may also be used provided that they retain the inhibitory properties of the serine protease inhibitors. Those skilled in the art know how to find such fragments. Thus, this may be accomplished, for example, by a selected enzymatic cleavage of the compounds according to the invention. Side-chain modified amino acids may also be employed. N- or C-terminally modified polypeptides may also be used. In particular, phosphorylated, glycosylated, methylated, acetylated or similarly modified polypeptides can be employed provided that they do not substantially affect the activity of the serine protease inhibitors.

Derivatives of the nucleic acids according to the invention which have modified triplet structures in accordance with codon usage may also be used. In addition, nucleic acids according to the invention also include those which are more stable towards degradation by nucleases as compared with the native compounds, for example, the corresponding SODN derivatives usually employed in antisense technology to give the antisense structures a more stable design towards enzymatic attack.

Structures homologous to the polypeptides may also be used. In particular, these include polypeptide structures in which amino acids have been exchanged. Thus, for example, conservative amino acid substitutions in highly conserved regions can be considered as follows: any isoleucine, valine and leucine amino acid can be exchanged for any other of these amino acids, aspartate can be exchanged for glutamate and vice versa, glutamine for asparagine and vice versa, serine for threonine and vice versa. Conservative amino acid substitutions in less highly conserved regions can be as follows: Any of the amino acids isoleucine, valine and leucine for any other of these amino acids, aspartate for glutamate and, vice versa, glutamine for asparagine and vice versa, serine for threonine and vice versa, glycine for alanine and vice versa, alanine for valine and vice versa, any of the amino acids leucine, isoleucine or valine for methionine, lysine for arginine and vice versa, either of the amino acids arginine or lysine for either of the amino acids aspartate or glutamate, either of the amino acids arginine or lysine for histidine, glutamine for glutamate and vice versa, and asparagine for aspartate and vice versa.

SEQUENCE LISTING

```
<160> NUMBER OF SEQ ID NOS: 12

<210> SEQ ID NO 1
<211> LENGTH: 1064
<212> TYPE: PRT
<213> ORGANISM: mammalian

<400> SEQUENCE: 1

Met Lys Ile Ala Thr Val Ser Val Leu Leu Pro Leu Ala Leu Cys Leu
 1               5                  10                  15

Ile Gln Asp Ala Ala Ser Lys Asn Glu Asp Gln Glu Met Cys His Glu
                20                  25                  30

Phe Gln Ala Phe Met Lys Asn Gly Lys Leu Phe Cys Pro Gln Asp Lys
            35                  40                  45

Lys Phe Phe Gln Ser Leu Asp Gly Ile Met Phe Ile Asn Lys Cys Ala
        50                  55                  60

Thr Cys Lys Met Ile Leu Glu Lys Glu Ala Lys Ser Gln Lys Arg Ala
 65                  70                  75                  80

Arg His Leu Ala Arg Ala Pro Lys Ala Thr Ala Pro Thr Glu Leu Asn
                85                  90                  95

Cys Asp Asp Phe Lys Lys Gly Glu Arg Asp Gly Asp Phe Ile Cys Pro
            100                 105                 110

Asp Tyr Tyr Glu Ala Val Cys Gly Thr Asp Gly Lys Thr Tyr Asp Asn
        115                 120                 125

Arg Cys Ala Leu Cys Ala Glu Asn Ala Lys Thr Gly Ser Gln Ile Gly
```

-continued

```
            130                 135                 140
Val Lys Ser Glu Gly Glu Cys Lys Ser Asn Pro Glu Gln Asp Val
145                 150                 155                 160

Cys Ser Ala Phe Arg Pro Phe Val Arg Asp Gly Arg Leu Gly Cys Thr
                165                 170                 175

Arg Glu Asn Asp Pro Val Leu Gly Pro Asp Gly Lys Thr His Gly Asn
                180                 185                 190

Lys Cys Ala Met Cys Ala Glu Leu Phe Leu Lys Glu Ala Glu Asn Ala
                195                 200                 205

Lys Arg Glu Gly Glu Thr Arg Ile Arg Arg Asn Ala Glu Lys Asp Phe
                210                 215                 220

Cys Lys Glu Tyr Glu Lys Gln Val Arg Asn Gly Arg Leu Phe Cys Thr
225                 230                 235                 240

Arg Glu Ser Asp Pro Val Arg Gly Pro Asp Gly Arg Met His Gly Asn
                245                 250                 255

Lys Cys Ala Leu Cys Ala Glu Ile Phe Lys Arg Arg Phe Ser Glu Glu
                260                 265                 270

Asn Ser Lys Thr Asp Gln Asn Leu Gly Lys Ala Glu Glu Lys Thr Lys
                275                 280                 285

Val Lys Arg Glu Ile Val Lys Leu Cys Ser Gln Tyr Gln Asn Gln Ala
                290                 295                 300

Lys Asn Gly Ile Leu Phe Cys Thr Arg Glu Asn Asp Pro Ile Arg Gly
305                 310                 315                 320

Pro Asp Gly Lys Met His Gly Asn Leu Cys Ser Met Cys Gln Val Tyr
                325                 330                 335

Phe Gln Ala Glu Asn Glu Glu Lys Lys Lys Ala Glu Ala Arg Ala Arg
                340                 345                 350

Asn Lys Arg Glu Ser Gly Lys Ala Thr Ser Tyr Ala Glu Leu Cys Asn
                355                 360                 365

Glu Tyr Arg Lys Leu Val Arg Asn Gly Lys Leu Ala Cys Thr Arg Glu
                370                 375                 380

Asn Asp Pro Ile Gln Gly Pro Asp Gly Lys Val His Gly Asn Thr Cys
385                 390                 395                 400

Ser Met Cys Glu Val Phe Phe Gln Ala Glu Glu Glu Lys Lys Lys
                405                 410                 415

Lys Glu Gly Glu Ser Arg Asn Lys Arg Gln Ser Lys Ser Thr Ala Ser
                420                 425                 430

Phe Glu Glu Leu Cys Ser Glu Tyr Arg Lys Ser Arg Lys Asn Gly Arg
                435                 440                 445

Leu Phe Cys Thr Arg Glu Asn Asp Pro Ile Gln Gly Pro Asp Gly Lys
                450                 455                 460

Met His Gly Asn Thr Cys Ser Met Cys Glu Ala Phe Phe Gln Gln Glu
465                 470                 475                 480

Glu Arg Ala Arg Ala Lys Ala Lys Arg Glu Ala Lys Glu Ile Cys
                485                 490                 495

Ser Glu Phe Arg Asp Gln Val Arg Asn Gly Thr Leu Ile Cys Thr Arg
                500                 505                 510

Glu His Asn Pro Val Arg Gly Pro Asp Gly Lys Met His Gly Asn Lys
                515                 520                 525

Cys Ala Met Cys Ala Ser Val Phe Lys Leu Glu Glu Glu Lys Lys
                530                 535                 540

Asn Asp Lys Glu Glu Lys Gly Lys Val Glu Ala Glu Lys Val Lys Arg
545                 550                 555                 560
```

-continued

Glu Ala Val Gln Glu Leu Cys Ser Glu Tyr Arg His Tyr Val Arg Asn
            565                 570                 575
Gly Arg Leu Pro Cys Thr Arg Glu Asn Asp Pro Ile Glu Gly Leu Asp
            580                 585                 590
Gly Lys Ile His Gly Asn Thr Cys Ser Met Cys Glu Ala Phe Phe Gln
            595                 600                 605
Gln Glu Ala Lys Glu Lys Glu Arg Ala Glu Pro Arg Ala Lys Val Lys
            610                 615                 620
Arg Glu Ala Glu Lys Glu Thr Cys Asp Glu Phe Arg Arg Leu Leu Gln
625                 630                 635                 640
Asn Gly Lys Leu Phe Cys Thr Arg Glu Asn Asp Pro Val Arg Gly Pro
            645                 650                 655
Asp Gly Lys Thr His Gly Asn Lys Cys Ala Met Cys Lys Ala Val Phe
            660                 665                 670
Gln Lys Glu Asn Glu Glu Arg Lys Arg Lys Glu Glu Glu Asp Gln Arg
            675                 680                 685
Asn Ala Ala Gly His Gly Ser Ser Gly Gly Gly Gly Asn Thr Gln
690                 695                 700
Asp Glu Cys Ala Glu Tyr Gln Glu Gln Met Lys Asn Gly Arg Leu Ser
705                 710                 715                 720
Cys Thr Arg Glu Ser Asp Pro Val Arg Asp Ala Asp Gly Lys Ser Tyr
            725                 730                 735
Asn Asn Gln Cys Thr Met Cys Lys Ala Lys Leu Glu Arg Glu Ala Glu
            740                 745                 750
Arg Lys Asn Glu Tyr Ser Arg Ser Arg Ser Asn Gly Thr Gly Ser Glu
            755                 760                 765
Ser Gly Lys Asp Thr Cys Asp Glu Phe Arg Ser Gln Met Lys Asn Gly
            770                 775                 780
Lys Leu Ile Cys Thr Arg Glu Ser Asp Pro Val Arg Gly Pro Asp Gly
785                 790                 795                 800
Lys Thr His Gly Asn Lys Cys Thr Met Cys Lys Glu Lys Leu Glu Arg
            805                 810                 815
Glu Ala Ala Glu Lys Lys Lys Glu Asp Glu Asp Arg Ser Asn Thr
            820                 825                 830
Gly Glu Arg Ser Asn Thr Gly Glu Arg Ser Asn Asp Lys Glu Asp Leu
            835                 840                 845
Cys Arg Glu Phe Arg Ser Met Gln Arg Asn Gly Lys Leu Ile Cys Thr
            850                 855                 860
Arg Glu Asn Asn Pro Val Arg Gly Pro Tyr Gly Lys Met His Ile Asn
865                 870                 875                 880
Lys Cys Ala Met Cys Gln Ser Ile Phe Asp Arg Glu Ala Asn Glu Arg
            885                 890                 895
Lys Lys Lys Asp Glu Lys Ser Ser Lys Pro Ser Asn Asn Ala
            900                 905                 910
Lys Asp Glu Cys Ser Glu Phe Arg Asn Tyr Ile Arg Asn Asn Glu Leu
            915                 920                 925
Ile Cys Pro Arg Glu Asn Asp Pro Val His Gly Ala Asp Gly Lys Phe
            930                 935                 940
Tyr Thr Asn Lys Cys Tyr Met Cys Arg Ala Val Phe Leu Thr Glu Ala
945                 950                 955                 960
Leu Glu Arg Ala Lys Leu Gln Glu Lys Pro Ser His Val Arg Ala Ser
            965                 970                 975

```
Gln Glu Glu Asp Ser Pro Asp Ser Phe Ser Ser Leu Asp Ser Glu Met
                980                 985                 990

Cys Lys Asp Tyr Arg Val Leu Pro Arg Ile Gly Tyr Leu Cys Pro Lys
            995                 1000                1005

Asp Leu Lys Pro Val Cys Gly Asp Gly Gln Thr Tyr Asn Asn Pro
    1010                1015                1020

Cys Met Leu Cys His Glu Asn Leu Ile Arg Gln Thr Asn Thr His Ile
1025                1030                1035                1040

Arg Ser Thr Gly Lys Cys Glu Glu Ser Ser Thr Pro Gly Thr Thr Ala
                1045                1050                1055

Ala Ser Met Pro Pro Ser Asp Glu
            1060

<210> SEQ ID NO 2
<211> LENGTH: 35
<212> TYPE: PRT
<213> ORGANISM: mammalian

<400> SEQUENCE: 2

Ser Ala Phe Arg Pro Phe Val Arg Asp Gly Arg Leu Gly Cys Thr Arg
1               5                   10                  15

Glu Asn Asp Pro Val Leu Gly Pro Asp Gly Lys Thr His Gly Asn Lys
            20                  25                  30

Cys Ala Met
        35

<210> SEQ ID NO 3
<211> LENGTH: 35
<212> TYPE: PRT
<213> ORGANISM: mammalian

<400> SEQUENCE: 3

Asn Glu Tyr Arg Lys Leu Val Arg Asn Gly Lys Leu Ala Cys Thr Arg
1               5                   10                  15

Glu Asn Asp Pro Ile Gln Gly Pro Asp Gly Lys Val His Gly Asn Thr
            20                  25                  30

Cys Ser Met
        35

<210> SEQ ID NO 4
<211> LENGTH: 35
<212> TYPE: PRT
<213> ORGANISM: mammalian

<400> SEQUENCE: 4

Arg Glu Phe Arg Ser Met Gln Arg Asn Gly Lys Leu Ile Cys Thr Arg
1               5                   10                  15

Glu Asn Asn Pro Val Arg Gly Pro Tyr Gly Lys Met His Ile Asn Lys
            20                  25                  30

Cys Ala Met
        35

<210> SEQ ID NO 5
<211> LENGTH: 35
<212> TYPE: PRT
<213> ORGANISM: mammalian

<400> SEQUENCE: 5

Ser Glu Phe Arg Asn Tyr Ile Arg Asn Asn Glu Leu Ile Cys Pro Arg
1               5                   10                  15
```

```
Glu Asn Asp Pro Val His Gly Ala Asp Gly Lys Phe Tyr Thr Asn Lys
             20                  25                  30

Cys Tyr Met
         35

<210> SEQ ID NO 6
<211> LENGTH: 52
<212> TYPE: PRT
<213> ORGANISM: mammalian

<400> SEQUENCE: 6

Lys Asp Tyr Arg Val Leu Pro Arg Ile Gly Tyr Leu Cys Pro Lys Asp
 1               5                  10                  15

Leu Lys Pro Val Cys Gly Asp Asp Gly Gln Thr Tyr Asn Asn Pro Cys
             20                  25                  30

Met Leu Cys His Glu Asn Leu Ile Arg Gln Thr Asn Thr His Ile Arg
         35                  40                  45

Ser Thr Gly Lys
         50

<210> SEQ ID NO 7
<211> LENGTH: 3532
<212> TYPE: DNA
<213> ORGANISM: mammalian
<220> FEATURE:
<221> NAME/KEY: CDS
<222> LOCATION: (44)..(3235)

<400> SEQUENCE: 7
```

| | |
|---|---:|
| tatgcatgga gtggacctgt aggcgacttg catcgtcttc aac atg aag ata gcc<br>                                                    Met Lys Ile Ala<br>                                                     1 | 55 |
| aca gtg tca gtg ctt ctg ccc ttg gct ctt tgc ctc ata caa gat gct<br>Thr Val Ser Val Leu Leu Pro Leu Ala Leu Cys Leu Ile Gln Asp Ala<br>  5              10                  15                  20 | 103 |
| gcc agt aag aat gaa gat cag gaa atg tgc cat gaa ttt cag gca ttt<br>Ala Ser Lys Asn Glu Asp Gln Glu Met Cys His Glu Phe Gln Ala Phe<br>             25                  30                  35 | 151 |
| atg aaa aat gga aaa ctg ttc tgt ccc cag gat aag aaa ttt ttt caa<br>Met Lys Asn Gly Lys Leu Phe Cys Pro Gln Asp Lys Lys Phe Phe Gln<br>         40                  45                  50 | 199 |
| agt ctt gat gga ata atg ttc atc aat aaa tgt gcc acg tgc aaa atg<br>Ser Leu Asp Gly Ile Met Phe Ile Asn Lys Cys Ala Thr Cys Lys Met<br>     55                  60                  65 | 247 |
| ata ctg gaa aaa gaa gca aaa tca cag aag agg gcc agg cat tta gca<br>Ile Leu Glu Lys Glu Ala Lys Ser Gln Lys Arg Ala Arg His Leu Ala<br> 70                  75                  80 | 295 |
| aga gct ccc aag gct act gcc cca aca gag ctg aat tgt gat gat ttt<br>Arg Ala Pro Lys Ala Thr Ala Pro Thr Glu Leu Asn Cys Asp Asp Phe<br> 85                  90                  95                 100 | 343 |
| aaa aaa gga gaa aga gat ggg gat ttt atc tgt cct gat tat tat gaa<br>Lys Lys Gly Glu Arg Asp Gly Asp Phe Ile Cys Pro Asp Tyr Tyr Glu<br>                 105                 110                 115 | 391 |
| gct gtt tgt ggc aca gat ggg aaa aca tat gac aac aga tgt gca ctg<br>Ala Val Cys Gly Thr Asp Gly Lys Thr Tyr Asp Asn Arg Cys Ala Leu<br>             120                 125                 130 | 439 |
| tgt gct gag aat gcg aaa acc ggg tcc caa att ggt gta aaa agt gaa<br>Cys Ala Glu Asn Ala Lys Thr Gly Ser Gln Ile Gly Val Lys Ser Glu<br>         135                 140                 145 | 487 |
| ggg gaa tgt aag agc agt aat cca gag cag gat gta tgc agt gct ttt | 535 |

-continued

```
Gly Glu Cys Lys Ser Ser Asn Pro Glu Gln Asp Val Cys Ser Ala Phe
    150                 155                 160 cgg ccc ttt gtt aga gat gga aga ctt gga tgc aca agg gaa aat gat      583
Arg Pro Phe Val Arg Asp Gly Arg Leu Gly Cys Thr Arg Glu Asn Asp
165                 170                 175                 180 cct gtt ctt ggt cct gat ggg aag acg cat ggc aat aag tgt gca atg      631
Pro Val Leu Gly Pro Asp Gly Lys Thr His Gly Asn Lys Cys Ala Met
                185                 190                 195 tgt gct gag ctg ttt tta aaa gaa gct gaa aat gcc aag cga gag ggt      679
Cys Ala Glu Leu Phe Leu Lys Glu Ala Glu Asn Ala Lys Arg Glu Gly
            200                 205                 210 gaa act aga att cga cga aat gct gaa aag gat ttt tgc aag gaa tat      727
Glu Thr Arg Ile Arg Arg Asn Ala Glu Lys Asp Phe Cys Lys Glu Tyr
        215                 220                 225 gaa aaa caa gtg aga aat gga agg ctt ttt tgt aca cgg gag agt gat      775
Glu Lys Gln Val Arg Asn Gly Arg Leu Phe Cys Thr Arg Glu Ser Asp
    230                 235                 240 cca gtc cgt ggc cct gac ggc agg atg cat ggc aac aaa tgt gcc ctg      823
Pro Val Arg Gly Pro Asp Gly Arg Met His Gly Asn Lys Cys Ala Leu
245                 250                 255                 260 tgt gct gaa att ttc aag cgg cgt ttt tca gag gaa aac agt aaa aca      871
Cys Ala Glu Ile Phe Lys Arg Arg Phe Ser Glu Glu Asn Ser Lys Thr
                265                 270                 275 gat caa aat ttg gga aaa gct gaa gaa aaa act aaa gtt aaa aga gaa      919
Asp Gln Asn Leu Gly Lys Ala Glu Glu Lys Thr Lys Val Lys Arg Glu
            280                 285                 290 att gtg aaa ctc tgc agt caa tat caa aat cag gca aag aat gga ata      967
Ile Val Lys Leu Cys Ser Gln Tyr Gln Asn Gln Ala Lys Asn Gly Ile
        295                 300                 305 ctt ttc tgt acc aga gaa aat gac cct att cgt ggt cca gat ggg aaa     1015
Leu Phe Cys Thr Arg Glu Asn Asp Pro Ile Arg Gly Pro Asp Gly Lys
    310                 315                 320 atg cat ggc aac ttg tgt tcc atg tgt caa gtc tac ttc caa gca gaa     1063
Met His Gly Asn Leu Cys Ser Met Cys Gln Val Tyr Phe Gln Ala Glu
325                 330                 335                 340 aat gaa gaa aag aaa aag gct gaa gca cga gct aga aac aaa aga gaa     1111
Asn Glu Glu Lys Lys Lys Ala Glu Ala Arg Ala Arg Asn Lys Arg Glu
                345                 350                 355 tct gga aaa gca acc tca tat gca gag ctt tgc aat gaa tat cga aag     1159
Ser Gly Lys Ala Thr Ser Tyr Ala Glu Leu Cys Asn Glu Tyr Arg Lys
            360                 365                 370 ctt gtg agg aac gga aaa ctt gct tgc acc aga gag aac gat cct atc     1207
Leu Val Arg Asn Gly Lys Leu Ala Cys Thr Arg Glu Asn Asp Pro Ile
        375                 380                 385 cag ggc cca gat ggg aaa gtg cac ggc aac acc tgc tcc atg tgt gag     1255
Gln Gly Pro Asp Gly Lys Val His Gly Asn Thr Cys Ser Met Cys Glu
    390                 395                 400 gtc ttc ttc caa gca gaa gaa gaa gaa aag aaa aag aag gaa ggc gaa     1303
Val Phe Phe Gln Ala Glu Glu Glu Glu Lys Lys Lys Lys Glu Gly Glu
405                 410                 415                 420 tca aga aac aaa aga caa tct aag agt aca gct tcc ttt gag gag ttg     1351
Ser Arg Asn Lys Arg Gln Ser Lys Ser Thr Ala Ser Phe Glu Glu Leu
                425                 430                 435 tgt agt gaa tac cgc aaa tcc agg aaa aac gga cgg ctt ttt tgc acc     1399
Cys Ser Glu Tyr Arg Lys Ser Arg Lys Asn Gly Arg Leu Phe Cys Thr
            440                 445                 450 aga gag aat gac ccc atc cag ggc cca gat ggg aaa atg cat ggc aac     1447
Arg Glu Asn Asp Pro Ile Gln Gly Pro Asp Gly Lys Met His Gly Asn
        455                 460                 465
```

-continued

| | | |
|---|---|---|
| acc tgc tcc atg tgt gag gcc ttc ttt caa caa gaa gaa aga gca aga<br>Thr Cys Ser Met Cys Glu Ala Phe Phe Gln Gln Glu Glu Arg Ala Arg<br>470　　　　　　475　　　　　　　　480 | | 1495 |
| gca aag gct aaa aga gaa gct gca aag gaa atc tgc agt gaa ttt cgg<br>Ala Lys Ala Lys Arg Glu Ala Ala Lys Glu Ile Cys Ser Glu Phe Arg<br>485　　　　　　　　490　　　　　　495　　　　　　　　500 | | 1543 |
| gac caa gtg agg aat gga aca ctt ata tgc acc agg gag cat aat cct<br>Asp Gln Val Arg Asn Gly Thr Leu Ile Cys Thr Arg Glu His Asn Pro<br>　　　　　　505　　　　　　　　510　　　　　　515 | | 1591 |
| gtc cgt gga cca gat ggc aaa atg cat gga aac aag tgt gcc atg tgt<br>Val Arg Gly Pro Asp Gly Lys Met His Gly Asn Lys Cys Ala Met Cys<br>520　　　　　　　　525　　　　　　530 | | 1639 |
| gcc agt gtg ttc aaa ctt gaa gaa gaa gag aag aaa aat gat aaa gaa<br>Ala Ser Val Phe Lys Leu Glu Glu Glu Glu Lys Lys Asn Asp Lys Glu<br>535　　　　　　　　540　　　　　　545 | | 1687 |
| gaa aaa ggg aaa gtt gag gct gaa aaa gtt aag aga gaa gca gtt cag<br>Glu Lys Gly Lys Val Glu Ala Glu Lys Val Lys Arg Glu Ala Val Gln<br>550　　　　　　555　　　　　　　　560 | | 1735 |
| gag ctg tgc agt gaa tat cgt cat tat gtg agg aat gga cga ctc ccc<br>Glu Leu Cys Ser Glu Tyr Arg His Tyr Val Arg Asn Gly Arg Leu Pro<br>565　　　　　　　　570　　　　　　575　　　　　　　　580 | | 1783 |
| tgt acc aga gag aat gat cct att gag ggt cta gat ggg aaa atc cac<br>Cys Thr Arg Glu Asn Asp Pro Ile Glu Gly Leu Asp Gly Lys Ile His<br>　　　　　　585　　　　　　　　590　　　　　　595 | | 1831 |
| ggc aac acc tgc tcc atg tgt gaa gcc ttc ttc cag caa gaa gca aaa<br>Gly Asn Thr Cys Ser Met Cys Glu Ala Phe Phe Gln Gln Glu Ala Lys<br>600　　　　　　　　605　　　　　　610 | | 1879 |
| gaa aaa gaa aga gct gaa ccc aga gca aaa gtc aaa aga gaa gct gaa<br>Glu Lys Glu Arg Ala Glu Pro Arg Ala Lys Val Lys Arg Glu Ala Glu<br>615　　　　　　620　　　　　　　　625 | | 1927 |
| aag gag aca tgc gat gaa ttt cgg aga ctt ttg caa aat gga aaa ctt<br>Lys Glu Thr Cys Asp Glu Phe Arg Arg Leu Leu Gln Asn Gly Lys Leu<br>630　　　　　　　　635　　　　　　640 | | 1975 |
| ttc tgc aca aga gaa aat gat cct gtg cgt ggc cca gat ggc aag acc<br>Phe Cys Thr Arg Glu Asn Asp Pro Val Arg Gly Pro Asp Gly Lys Thr<br>645　　　　　　650　　　　　　　　655　　　　　　660 | | 2023 |
| cat ggc aac aag tgt gcc atg tgt aag gca gtc ttc cag aaa gaa aat<br>His Gly Asn Lys Cys Ala Met Cys Lys Ala Val Phe Gln Lys Glu Asn<br>　　　　　　665　　　　　　　　670　　　　　　675 | | 2071 |
| gag gaa aga aag agg aaa gaa gag gaa gat cag aga aat gct gca gga<br>Glu Glu Arg Lys Arg Lys Glu Glu Glu Asp Gln Arg Asn Ala Ala Gly<br>680　　　　　　　　685　　　　　　690 | | 2119 |
| cat ggt tcc agt ggt ggt gga gga gga aac act cag gac gaa tgt gct<br>His Gly Ser Ser Gly Gly Gly Gly Asn Thr Gln Asp Glu Cys Ala<br>695　　　　　　700　　　　　　　　705 | | 2167 |
| gag tat cag gaa caa atg aaa aat gga aga ctc agc tgt act cgg gag<br>Glu Tyr Gln Glu Gln Met Lys Asn Gly Arg Leu Ser Cys Thr Arg Glu<br>710　　　　　　　　715　　　　　　720 | | 2215 |
| agt gat cct gta cgt gat gct gat ggc aaa tcg tac aac aat cag tgt<br>Ser Asp Pro Val Arg Asp Ala Asp Gly Lys Ser Tyr Asn Asn Gln Cys<br>725　　　　　　730　　　　　　　　735　　　　　　740 | | 2263 |
| acc atg tgt aaa gca aaa ttg gaa aga gaa gca gag aga aaa aat gag<br>Thr Met Cys Lys Ala Lys Leu Glu Arg Glu Ala Glu Arg Lys Asn Glu<br>　　　　　　745　　　　　　　　750　　　　　　755 | | 2311 |
| tat tct cgc tcc aga tca aat ggg act gga tca gaa tca ggg aag gat<br>Tyr Ser Arg Ser Arg Ser Asn Gly Thr Gly Ser Glu Ser Gly Lys Asp<br>760　　　　　　　　765　　　　　　770 | | 2359 |
| aca tgt gat gag ttt aga agc caa atg aaa aat gga aaa ctt atc tgc<br>Thr Cys Asp Glu Phe Arg Ser Gln Met Lys Asn Gly Lys Leu Ile Cys<br>775　　　　　　780　　　　　　　　785 | | 2407 |

-continued

| | |
|---|---|
| act cga gaa agt gac cct gtc cgg ggt cca gat ggc aag aca cat ggt<br>Thr Arg Glu Ser Asp Pro Val Arg Gly Pro Asp Gly Lys Thr His Gly<br>790                   795                   800 | 2455 |
| aat aag tgt act atg tgt aag gaa aaa ctg gaa agg gaa gca gct gaa<br>Asn Lys Cys Thr Met Cys Lys Glu Lys Leu Glu Arg Glu Ala Ala Glu<br>805                   810                   815                   820 | 2503 |
| aaa aaa aag aaa gag gat gaa gac agg agc aat aca gga gaa agg agc<br>Lys Lys Lys Lys Glu Asp Glu Asp Arg Ser Asn Thr Gly Glu Arg Ser<br>                   825                   830                   835 | 2551 |
| aat aca gga gaa agg agc aat gac aaa gag gat ctg tgt cgt gaa ttt<br>Asn Thr Gly Glu Arg Ser Asn Asp Lys Glu Asp Leu Cys Arg Glu Phe<br>840                   845                   850 | 2599 |
| cga agc atg cag aga aat gga aag ctt atc tgc acc aga gaa aat aac<br>Arg Ser Met Gln Arg Asn Gly Lys Leu Ile Cys Thr Arg Glu Asn Asn<br>                   855                   860                   865 | 2647 |
| cct gtt cga ggc cca tat ggc aag atg cac atc aat aaa tgt gct atg<br>Pro Val Arg Gly Pro Tyr Gly Lys Met His Ile Asn Lys Cys Ala Met<br>870                   875                   880 | 2695 |
| tgt cag agc atc ttt gat cga gaa gct aat gaa aga aaa aag aaa gat<br>Cys Gln Ser Ile Phe Asp Arg Glu Ala Asn Glu Arg Lys Lys Lys Asp<br>885                   890                   895                   900 | 2743 |
| gaa gag aaa tca agt agc aag ccc tca aat aat gca aag gat gag tgc<br>Glu Glu Lys Ser Ser Ser Lys Pro Ser Asn Asn Ala Lys Asp Glu Cys<br>                   905                   910                   915 | 2791 |
| agt gaa ttt cga aac tat ata agg aac aat gaa ctc atc tgc cct aga<br>Ser Glu Phe Arg Asn Tyr Ile Arg Asn Asn Glu Leu Ile Cys Pro Arg<br>920                   925                   930 | 2839 |
| gag aat gac cca gtg cac ggt gct gat gga aag ttc tat aca aac aag<br>Glu Asn Asp Pro Val His Gly Ala Asp Gly Lys Phe Tyr Thr Asn Lys<br>                   935                   940                   945 | 2887 |
| tgc tac atg tgc aga gct gtc ttt cta aca gaa gct ttg gaa agg gca<br>Cys Tyr Met Cys Arg Ala Val Phe Leu Thr Glu Ala Leu Glu Arg Ala<br>950                   955                   960 | 2935 |
| aag ctt caa gaa aag cca tcc cat gtt aga gct tct caa gag gaa gac<br>Lys Leu Gln Glu Lys Pro Ser His Val Arg Ala Ser Gln Glu Glu Asp<br>965                   970                   975                   980 | 2983 |
| agc cca gac tct ttc agt tct ctg gat tct gag atg tgc aaa gac tac<br>Ser Pro Asp Ser Phe Ser Ser Leu Asp Ser Glu Met Cys Lys Asp Tyr<br>                   985                   990                   995 | 3031 |
| cga gta ttg ccc agg ata ggc tat ctt tgt cca aag gat tta aag cct<br>Arg Val Leu Pro Arg Ile Gly Tyr Leu Cys Pro Lys Asp Leu Lys Pro<br>1000                  1005                  1010 | 3079 |
| gtc tgt ggt gac gat ggc caa acc tac aac aat cct tgc atg ctc tgt<br>Val Cys Gly Asp Asp Gly Gln Thr Tyr Asn Asn Pro Cys Met Leu Cys<br>                  1015                  1020                  1025 | 3127 |
| cat gaa aac ctg ata cgc caa aca aat aca cac atc cgc agt aca ggg<br>His Glu Asn Leu Ile Arg Gln Thr Asn Thr His Ile Arg Ser Thr Gly<br>1030                  1035                  1040 | 3175 |
| aag tgt gag gag agc agc acc cca gga acc acc gca gcc agc atg ccc<br>Lys Cys Glu Glu Ser Ser Thr Pro Gly Thr Thr Ala Ala Ser Met Pro<br>1045                  1050                  1055                  1060 | 3223 |
| ccg tct gac gaa tgacaggaag attgttgaaa gccatgaggg aaaaaataaa<br>Pro Ser Asp Glu | 3275 |
| ccccagttct gaatcaccta ccttcaccat ctgtatatac aaagaattct tcggagcttg | 3335 |
| tcttatttgc tatagaaaac aatacagagc ttttgggaat ggaatcactg attttcagtc | 3395 |
| ttttccattt ctttcctcct agaatctgtg atctgagggt ataaagacat ttccaccaag | 3455 |
| tttgagccct caaaatgtcc tgattacaat gctgtctgtc caactgcctg ttcaataaaa | 3515 |

-continued

```
gtaaactcag cagaaaa                                                     3532

<210> SEQ ID NO 8
<211> LENGTH: 105
<212> TYPE: DNA
<213> ORGANISM: mammalian

<400> SEQUENCE: 8
agtgcttttc ggccctttgt tagagatgga agacttggat gcacaaggga aaatgatcct        60
gttcttggtc ctgatgggaa gacgcatggc aataagtgtg caatg                       105

<210> SEQ ID NO 9
<211> LENGTH: 105
<212> TYPE: DNA
<213> ORGANISM: mammalian

<400> SEQUENCE: 9
aatgaatatc gaaagcttgt gaggaacgga aaacttgctt gcaccagaga gaacgatcct        60
atccagggcc cagatgggaa agtgcacggc aacacctgct ccatg                       105

<210> SEQ ID NO 10
<211> LENGTH: 99
<212> TYPE: DNA
<213> ORGANISM: mammalian

<400> SEQUENCE: 10
cgtgaatttc gaagcatgca gagaaatgga aagcttatct gcaccagaga aaataaccct        60
gttcgaggcc catatggcaa gatgcacatc aataaatgt                              99

<210> SEQ ID NO 11
<211> LENGTH: 105
<212> TYPE: DNA
<213> ORGANISM: mammalian

<400> SEQUENCE: 11
agtgaatttc gaaactatat aaggaacaat gaactcatct gccctagaga gaatgaccca        60
gtgcacggtg ctgatggaaa gttctataca aacaagtgct acatg                       105

<210> SEQ ID NO 12
<211> LENGTH: 156
<212> TYPE: DNA
<213> ORGANISM: mammalian

<400> SEQUENCE: 12
aaagactacc gagtattgcc caggataggc tatctttgtc caaaggattt aaagcctgtc        60
tgtggtgacg atggccaaac ctacaacaat ccttgcatgc tctgtcatga aaacctgata       120
cgccaaacaa atacacacat ccgcagtaca gggaag                                156
```

What is claimed is:

1. A serine protease inhibitor having the amino acid sequence according to SEQ ID NO: 1.

2. A medicament containing at least one serine protease inhibitor according to claim 1, optionally together with a pharmaceutical vehicle.

3. The medicament according to claim 2, containing from 0.01 to 1000 mg of the serine protease inhibitor per kg of body weight of a patient in need thereof.

4. A method of using the serine protease inhibitor according to claim 1 comprising administering the serine protease inhibitor to a patient in need thereof as a medicament for the treatment of acute or chronic cervix inflammations, inflammations of Bartholin's glands or other vaginal regions, tonsillitis, pharyngitis or laryngitis, or acute or chronic inflammatory processes accompanied by excessive formation of mucus the resulting acute emergency situations, postoperative bleedings due to hyperfibrinolysis or for the prophylaxis of lung emphysema formation because of deficiencies of $\alpha_1$-proteinase inhibitor.

* * * * *